United States Patent [19]
Bordt et al.

[11] Patent Number: 5,200,179
[45] Date of Patent: Apr. 6, 1993

[54] VACCINE

[75] Inventors: Dale Bordt; Hans Draayer, both of Jacksonville, Ill.

[73] Assignee: Beecham Group p.l.c., Middlesex, England

[21] Appl. No.: 655,254

[22] Filed: Feb. 13, 1991

Related U.S. Application Data

[63] Continuation of Ser. No. 243,251, Sep. 14, 1988, abandoned, which is a continuation of Ser. No. 101,822, Sep. 28, 1987, abandoned.

[51] Int. Cl.$^5$ ...................... A61K 39/12; A61K 39/02
[52] U.S. Cl. ......................................... 424/89; 424/92
[58] Field of Search ..................... 424/89, 92; 514/888

[56] References Cited
U.S. PATENT DOCUMENTS 3,585,108  6/1971  Welter .................................. 424/89

FOREIGN PATENT DOCUMENTS 0046409  2/1982  European Pat. Off. .
0287210  10/1988  European Pat. Off. .

OTHER PUBLICATIONS

Chemical Abstracts (79: 62042e) 1973.
Chemical Abstracts (100: 33541p) 1984.
Chemical Abstracts (105: 206030e) 1986.
Chemical Abstracts (111: 70953x) 1989.

Primary Examiner—Frederick E. Waddell
Assistant Examiner—K. Weddington
Attorney, Agent, or Firm—Hopgood, Calimafde, Kalil, Blaustein & Judlowe

[57] ABSTRACT

Sterile pharmaceutical compositions for use in therapy especially inactivated vaccines for use in prophylaxis, are prepared by inactivating a live virus or bacterium with ascorbic acid and/or a salt thereof in the presence of oxygen and a source of heavy metal ions. Methods of treating animals, including humans, with such compositions are also disclosed.

14 Claims, No Drawings

VACCINE

This application is a continuation, of application Ser. No. 07/243,251, filed Sep. 14, 1988, now abandoned which is a continuation of application 07/101,822, filed Sep. 28, 1987, now abandoned.

This invention relates to a process for preparing a pharmaceutical composition which is substantially free from live viruses or bacteria. The invention also relates to pharmaceutical compositions produced by the process, and to their use in therapy. The invention is of particular value in the field of inactivated vaccines for use in prophylaxis.

In the field of medicine, it is frequently necessary or desirable to render pharmaceutical compositions for administration to animals including man free of potentially harmful live viruses or bacteria. Such an inactivation step may be particularly important when an inactivated (or 'killed') vaccine is required.

A number of methods are known for inactivating viruses or bacteria, such as treatment with $\beta$-propiolactone, formaldehyde or ethyleneimine. Such reagents are, however, potentially hazardous to handle and safer techniques are desirable.

The inactivation of certain viral diagnostic antigens by ascorbic acid undergoing auto-oxidation catalysed by cupric sulphate has been reported (L. A. White et al., *J. Clinical Microbiology*, 1986, 24. 527–531). Surprisingly, we have found that viruses and bacteria may be inactivated in pharmaceutical compositions by similar treatment.

The present invention provides a pharmaceutical composition which is substantially free from live viruses or bacteria and contains an inactivated virus or bacterium together with a pharmaceutically acceptable carrier, characterised in that the inactivated virus or bacterium was prepared by inactivating a live virus or bacterium with ascorbic acid and/or a salt thereof in the presence of oxygen and a source of heavy metal ions.

The invention also provides a substance or composition which is substantially free from live viruses or bacteria and prepared by a method which comprises inactivating a live virus or bacterium with ascorbic acid and/or a salt thereof in the presence of oxygen and a source of metal ions, for use in therapy.

As used herein the term 'therapy' includes prophylaxis.

In a further aspect the invention provides a process for preparing a pharmaceutical composition, which process comprises admixing an inactivated virus or bacterium with a pharmaceutically acceptable carrier, characterized in that the inactivated virus or bacterium was prepared by inactivating a live virus or bacterium with ascorbic acid and/or a salt thereof in the presence of oxygen and a source of heavy metal ions.

In yet a further aspect the invention provides a process for preparing a pharmaceutical composition which is substantially free from live viruses or bacteria, which process comprises inactivating a live virus or bacterium with ascorbic acid and/or a salt thereof in the presence of oxygen and a source of heavy metal ions.

In yet another aspect of the invention, there is provided a method of preventing disease in animals. including humans, which method comprises administering to an animal in need thereof an effective amount of a pharmaceutical composition according to the invention.

The advantage of the invention is that carcinogenic or otherwise hazardous reagents known in the art for viral inactivation, such as $\beta$-propiolactone, formaldehyde and ethyleneimine, are no longer required, thereby making the inactivation procedure safer.

The pharmaceutical composition according to the invention may be any medicament formulated for administration by any suitable route, for example by parenteral or topical application.

In a preferred aspect the pharmaceutical composition is an inactivated vaccine against viral or bacterial infections, for example an inactivated vaccine against transmissible gastroenteritis virus of swine (TGEV), parvovirus, members of the Herpes virus group, for example pseudorabies virus (PRV) and infectious bovine rhinotracheitis (IBR) virus, paramyxo, parainfluenza-3, bovine coronavirus and bovine repiratory syncytial virus.

Accordingly in yet another aspect the invention provides the use of a substance or composition which is substantially free from live viruses or bacteria and prepared by a method which comprises inactivating a live virus or bacterium with ascorbic acid and/or a salt thereof in the presence of oxygen and a source of heavy metal ions, in the manufacture of an inactivated vaccine composition for the prophylaxis of viral or bacterial infections.

In one preferred aspect the inactivated vaccine is a vaccine against transmissible gastroenteritis virus of swine.

In another preferred aspect the inactivated vaccine is a combination vaccine against more than one virus, for example up to 5, preferably up to 3 viruses. A preferred vaccine of this type is that against infectious bovine rhinotracheitis-virus diarrheaparainfluenza-3.

It will be understood that other active agents may be present in the pharmaceutical composition according to the invention.

The inactivated vaccine may optionally contain adjuvants including, for example, aluminium hydroxide (for example 2–25%, preferably 5–25% by weight), saponin (for example 0.5–1.5 mg./dose) and Freund's incomplete adjuvant (typical water in oil emulsion).

The vaccine may be administered in a dose of at least 1.9 logs of inactivated virus particles per dose, preferably at least 1,000 virus particles (3 logs of virus particles) per dose. Normally the inactivated vaccine will be administered in at least 4 logs of inactivated virus particles per dose.

Suitable forms of ascorbic acid include the alkali metal or alkaline earth metal salts, for example the sodium, potassium or calcium salts, or ascorbic acid itself.

A preferred salt is the sodium salt.

A suitable ascorbate concentration for use in the inactivation step is in the range 1–10 mM, preferably 2.0 mM–6.0 mM, for example 2.5 mM.

Suitable sources of heavy metal ions include salts of copper, iron and zinc and mercury-containing compounds.

One preferred heavy metal ion is the cupric ($Cu^{2+}$) ion, a convenient source of which is cupric sulphate.

Another preferred heavy metal ion is mercury, convenient sources of which are organo-mercury compounds, especially ethylmercurithiosalicylic acid, sodium salt (thimerosal).

The heavy metal ion is present in a catalytic amount, a suitable concentration for use in the inactivation step being in the range 0.01 mM to 0.1 mM, preferably 0.015 mM to 0.05 mM, for example 0.022 mM.

The presence of oxygen is essential and is conveniently provided by adequate aeration.

Normally the inactivation step is allowed to proceed at between 1 and 54° C., preferably at about 37° C., until an inactivation test proves satisfactory. The required inactivation period is typically in the range 10–100 hours, generally about 48–72 hours.

For the inactivation of certain viruses, for example parvovirus and rotavirus, a second addition of ascorbic acid may be required to complete the inactivation process.

In addition, other agents known to inactivate viruses may optionally be added to complete the inactivation process. One such reagent is saponin as described in, for example, Vet. Med. Nauki, 1980, 17(3), 45–55 (A. Motovski et al.), which may, for example, be added at a concentration of 0.5 mg/ml about 72 hours after ascorbic acid addition. Such a procedure has proved especially useful for the inactivation of enveloped viruses such as viruses of the Herpes group including PRV and IBR.

The progress of the inactivation process may conveniently be monitored by measuring the viability of the virus at intervals using any convenient method, for example by a rabbit indirect fluorescent antibody test to determine residual virus titre.

In the production of inactivated vaccines stabilising agents may advantageously be added before, during, or after the inactivation process to enhance antigen stability. Suitable stabilising agents include bovine serum albumin or other serum types.

A preferred stabilising agent is bovine (foetal) calf serum.

Preferably the stabilising agent is added before or during the inactivation process.

The stabilising agent is suitably present in a concentration of 0.5 to 5% v/v, preferably 1 to 3%, more preferably about 2% v/v.

The following Examples illustrate the invention.

EXAMPLES

In the following Examples stock solutions of L-ascorbic acid and cupric sulphate were prepared as follows.

Preparation 1

L-ascorbic acid-(AA) working solution is prepared by dissolving 100 grams of AA per 1 liter of distilled water (100 mg/ml). The reagent is sterilized, using a 0.20μ Micron filter assembly, and stored frozen.

Preparation 2

Cupric sulphate working solution (0.5 mg/ml) is prepared by dissolving 0.5 g cupric sulphate in 1 liter of distilled water and autoclaving at 121° C. for 10–15 minutes. The solution is stored at 4° C.

Example 1

Inactivation of Infectious Bovine Rhinotracheitis (IBR) Virus

Under constant agitation, L-ascorbic acid, sodium salt, (100 mg/ml) was slowly added to the virus fluids to a final concentration of 1 mg/ml, followed immediately by the addition of cupric sulphate (0.5 mg/ml stock) to a final concentration of 0.55 μg/ml. The fluids were maintained at 37° C. under constant agitation and aeration for 72 to 80 hours.

Following the first phase of inactivation, the fluids were placed in a cooler (1.5°–7° C.) and allowed to come to a temperature of 1.5°–7° C. The pH was adjusted to 7.2–7.4 and saponin (20 mg/ml) was slowly added to the virus fluids under constant agitation to a final concentration of 0.5 mg/ml followed by thimerosal (2.5%) to a final concentration of 0.01%. The fluids were maintained at 1.5°–7° C. under constant agitation for three days. The inactivated fluids were stored at 1.5°–7° C.

Example 2

Inactivation of Parainfluenza-3 (PI-3) Virus

Thimerosal (2.5%) was added to a final concentration of 0.01%, and the pH of the fluids adjusted to 7.2–7.4 with 10N NaOH. Under constant agitation, L-Ascorbic acid (100 mg/ml) was slowly added to the virus fluids to a final concentration of 1 mg/ml. The fluids were maintained at 37° C. under constant agitation and aeration for 40–48 hours.

Following the first phase of inactivation, the fluids were placed in a coller (1.5°–7° C.) and allowed to come to a temperature of 1.5°–7° C. The pH was adjusted to 7.2–7.4 and saponin (20 mg/ml) was slowly added to the virus fluids under constant agitation to a final concentration of 0.5 mg/ml. The fluids were maintained at 1.5°–7° C. under constant agitation for three days. The inactivated fluids were stored at 1.5°–7° C.

Example 3

Efficacy of inactivated IBR/BVD/PI-3 vaccine.

1. Materials and Methods

A. Animals

Twenty-four 300–500 lb cattle, housed together, with no vaccination history to any of the components contained in the vaccine were used. Cattle were susceptible to IBR, BVD and PI-3 with serum neutralization or plaque reduction titer of ≦1:2 except where noted.

Two experimental IBR/BVD/PT-3 vaccines were assembled according to Table 1.

The IBR and PI-3 fractions were inactivated as described in Examples 1 and 2.

TABLE 1

| IBR/BVD/PI-3 Serial A and B Formulation ($log_{10}$ $TCID_{50}$/ml) | | | |
|---|---|---|---|
| COMPO-NENT | PRE-INAC. LOT TITER | CALCULATED SERIAL A | TITER/DOSE SERIAL B |
| IBR | 7.7 | 7.9 | 7.6 |
| BVD | 6.9 | 7.1 | 7.1 |
| PI-3 | 7.3 | 7.5 | 7.3 |

Twenty-four calves were used in this study. Ten calves were vaccinated intramuscularly with a 5 ml dose of Serial A; 9 calves were vaccinated in a similar manner with Serial B; 5 calves were held as non-vaccinated susceptible controls. All vaccinated calves were likewise revaccinated 21 days after the first vaccination. Calves were monitored daily for any untoward signs of vaccination.

B. Serology

Calves' antibody titres were determined at the time of vaccination, challenge, and 14 days following challenge.

C. Challenge

Calves were challenged intranasally with IBR followed 3 weeks later with PI-3.

Calves were monitored daily for three days prior to challenge (one day for PI-3) and for 14 days following each challenge for gross clinical signs and rectal temperatures. Virus shedding was monitored for 10 days following challenge. Nasal swabs were passaged 2 successive times on EBK cells for virus isolation.

Two calves were eliminated from the study prior to PI-3 challenge; one calf developed upper respiratory stress following treatment with a sulfa bolus and 1 calf was compromised with an advanced case of foot rot. The following scoring system was used to evaluate post-challenge clinical symptoms.

| Score | Signs |
|---|---|
| 1 point | Clear nasal discharge, sneezing, nasal mucosal inflammation, cough, lacrimation, excess salivation, nasal lesions. |
| 2 points | Mucopurulent nasal discharge. |

2. Results

All calves remained healthy during the post vaccination observation period.

A. Serological Responses

Serologic results are summarized in Table 2.

Four calves vaccinated with serial B were found to have pre-existing IBR antibody titers. These calves were included in the study because of their susceptibility to PI-3. Contact controls remained seronegative to IBR throughout the study, indicating the absence of IBR infection. Nine out of 10 calves vaccinated with Serial A were seronegative to IBR at the time of second vaccination, the remaining calf had a titer of 1:5. The calves had developed a geometric mean antibody titer (GMAT) of $\geq 1:16$ by three weeks following second vaccination (range 1:7 to $\geq 1:32$). Vaccinated calves demonstrated an anamnestic response following challenge.

In general, calves vaccinated with both serials A and B demonstrated little or no PI-3 antibody response at the time of second vaccination. At the time of PI-3 challenge, six weeks after second vaccination, calves vaccinated with Serial A had a GMAT of $\geq 1:273.5$ and those with Serial B a GMAT of $\geq 356$ (range 1:21 to $\geq 1:512$).

Calves demonstrated BVD GMATs of $\geq 1:5106$ and $\geq 18023$ respectively for Serials A and B (range 1:915 to $\geq 1:62500$).

TABLE 2

Reciprocal Geometric Mean Antibody Titers
IBR/BVD/PI-3(KV) Immune Response Study

| Fraction | Vaccine | Weeks Post Vac. 0 | 3 | 6 | Post Challenge |
|---|---|---|---|---|---|
| IBR | A | <2 | ≦2 | ≧16 | ≧196 |
| IBR | B | N.A. | N.A. | ≧62 | ≧153 |
| IBR | Control | <2 | <2 | ≦4 | 14 |
| BVD | A | <2 | N.A. | ≧5106 | N.A. |
| BVD | B | <2 | N.A. | ≧18023 | N.A. |
| BVD | Control | <2 | N.A. | <4 | N.A. |
| PI-3 | A | <2 | ≦3.5 | ≧273.5 | ≧2048 |
| PI-3 | B | ≦2.3 | ≦2.5 | ≧356 | ≧2048 |
| PI-3 | Control | <2 | ≦2 | ≦2 | ≧16 |

N.A. = Not analysed

B. IBR Post-Challenge Evaluations

Duplicate titrations of IBR challenge virus conducted immediately following challenge, indicated the calves were challenged with $10^{8.0}$ TCID$_{50}$.

Calves vaccinated with Serial A demonstrated a significant ($p<0.05$) reduction in rectal temperatures on days 3 and 4 post-challenge when compared to the control group.

IBR virus isolations were monitored for 10 days following challenge. All calves were free of IBR virus prior to challenge. IBR virus was recovered from all non-vaccinated controls (100% recovery) throughout the 10 day period. A significant reduction in virus recovery was shown among vaccinates on day 9 ($p<0.05$) and day 10 ($p<0.01$) when compared to non-vaccinated controls.

Clinical signs among vaccine Group A and B and controls following IBR challenge were milder than expected; significant differences between the vaccine and control groups were not demonstrated. However, there were reductions in clinical points in the vaccinated animals.

C. PI-3 Post-Challenge Evaluation

Results of duplicate titrations, conducted immediately following challenge, indicated the calves were challenged with $10^{7.8}$ TCID$_{50}$ of PI-3.

Clinical signs of PI-3 infection were mild to inapparent.

All calves were free of PI-3 virus prior to challenge. PI-3 virus was isolated an average of 7.4 days/cow from the non-vaccinated controls, while virus was isolated an average of 2.9 and 4.3 days/cow from calves vaccinated with Serials A and B respectively. A dose response is evident when comparing the results obtained with Serial A to those obtained with Serial B. The reduction in virus shed among calves vaccinated with both Serials A and B was significant when compared to the non-vaccinated controls ($p<0.01$).

Example 4

Inactivation of Bovine Respiratory Syncytial Virus (BRSV)

Inactivation was carried out by the method described in Example 1.

Example 5

Inactivated Transmissible Gastroenteritis Virus of Swine (TGEV) Vaccines

Purdue strain TGE virus (ATCC VR-763) was passaged 4 times on pig kidney cells (designated PK0809) to produce a master seed virus which was then passaged 3 times in porcine kidney cells and twice in Crandell feline kidney cells (ATCC CCL 94). The virus was propagated at 35°-38° C. on the Crandell feline kidney cell line (ATCC CCL 94) in Eagle's MEM containing not more than 10% bovine serum.

Two small roller bottles containing confluent Crandell feline kidney cell (ATCC CCL 94) monolayers were inoculated with 1 ml of undiluted TGE master seed virus. After a 1-2 hour adsorption period the virus growth medium (Eagle's MEM containing not more than 2% bovine serum) was added and the virus was grown at 35°-38° C.

One roller bottle containing TGE virus prepared as described above above was frozen and thawed (titre samples taken) and inactivated as follows (the bulk virus should have a pre-inactivation titre of at least $10^{5.5}$ per dose):

The bulk virus was put in a 1 liter glass bottle and brought to 37° C. Sodium ascorbate stock solution (1% w/v) and cupric sulphate stock solution (1.1% w/v) were then added to bring the final concentration of ascorbate to 5.05 mM and the final concentration of cupric ions to 0.022 mM. The contents of the bottle were mixed with adequate aeration for 72 hours at 37° C. and then cooled to 4° C.

After proof of inactivation, the bulk virus was split and adjuvanted to give two inactivated vaccines as follows:

Vaccine A

One half of the inactivated bulk virus was treated with 10% aluminum hydroxide by stirring for 15-20 hours at 4° C.

Vaccine B

The other half of the inactivated bulk virus was adjuvanted as follows:

Solution 1 consists of 5 ml emulsifier added to 95 ml of Drakoil 6 VR.

Solution 2 consists of 2.5 ml Tween 80 added to 47.5 ml of killed TGE virus.

Solution 1 (21 ml) is added to Solution 2 (7 ml) and mixed using a Perfektum emulsifying needle prior to vaccination.

We claim:

1. A vaccine which is substantially free from live viruses or bacteria and contains an inactivated virus or bacterium together with a pharmaceutically acceptable carrier, wherein the inactivated virus or bacterium was prepared by inactivating a live virus or bacterium with ascorbic acid and/or a salt thereof in the presence of oxygen and a source of heavy metal ions.

2. A vaccine according to claim 1 useful against viruses selected from the group consisting of transmissible gastroenteritis virus of swine, parvovirus, members of the Herpes virus group, paramyxo, parainfluenza-3, bovine coronavirus, and bovine respiratory syncytial virus.

3. A vaccine according to claim 1 which is a combination vaccine against infectious bovine rhinotracheitis-virus diarrhea-parainfluenza-3.

4. A vaccine according to claim 1 which comprises a prophylactically effective amount of an inactivated bacterium and is an inactivated vaccine against bacteria.

5. A vaccine according to claim 1 prepared by a method in which the source of metal ions is selected from the group consisting of salts of copper, iron, zinc and mercury-containing compounds.

6. A vaccine according to claim 1 in which the source of metal ions comprises the mercury-containing compound thimerosal.

7. A vaccine according to claim 1 in which the live virus or bacterium was inactivated in a medium additionally comprising saponin.

8. A vaccine according to claim 1 in which the live virus or bacterium was inactivated in the presence of a stabilizing agent capable of enhancing antigen stability.

9. A vaccine as claimed in claim 8 in which the stabilizing agent is bovine (foetal) calf serum.

10. A process for preparing a vaccine, which process comprises admixing an inactivated virus or bacterium with a pharmaceutically acceptable carrier, wherein the inactivated virus or bacterium was prepared by inactivating a live virus or bacterium with ascorbic acid and/or a salt thereof in the presence of oxygen and a source of heavy metal ions.

11. A process for preparing a vaccine including an inactivated virus or bacterium which composition is substantially free from live viruses or bacteria, which process comprises inactivating a live virus or bacterium with ascorbic acid and/or a salt thereof in the presence of oxygen and a source of heavy metal ions.

12. A method of preventing disease in animals, including humans, which method comprises administering to an animal in need thereof an effective amount of a vaccine as defined in claim 1.

13. A method according to claim 12 in which the vaccine comprises an inactivated virus.

14. A method according to claim 12 in which the vaccine is a combination vaccine against infectious bovine rhinotracheitis-virus diarrhea-parainfluenza-3.

* * * * *